(12) United States Patent
Wei et al.

(10) Patent No.: US 11,911,529 B2
(45) Date of Patent: *Feb. 27, 2024

(54) HYGIENE SYSTEM FOR A PORTABLE PACKAGED FOOD CONTAINER

(71) Applicant: Ecolab USA Inc., Saint Paul, MN (US)

(72) Inventors: Wenbin Wei, Shanghai (CN); Ying Zhang, Shanghai (CN); Zhili Ding, Shanghai (CN); Huarong Yu, Shanghai (CN)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,566

(22) Filed: Mar. 25, 2022

(65) Prior Publication Data

US 2022/0211892 A1 Jul. 7, 2022

Related U.S. Application Data

(63) Continuation of application No. 16/941,285, filed on Jul. 28, 2020, now Pat. No. 11,285,231, which is a (Continued)

(51) Int. Cl.
*B65B 55/02* (2006.01)
*A61L 2/24* (2006.01)
(Continued)

(52) U.S. Cl.
CPC ................. *A61L 2/24* (2013.01); *A47J 47/14* (2013.01); *A61L 2/22* (2013.01); *B08B 9/08* (2013.01);
(Continued)

(58) Field of Classification Search
CPC .......... A61L 2/00; A61L 2/24; A61L 2202/16; A61L 2202/23; A47J 47/14; B08B 9/08;
(Continued)

(56) References Cited

U.S. PATENT DOCUMENTS 6,189,330 B1 2/2001 Retallick et al.
6,445,976 B1 9/2002 Ostro
(Continued)

FOREIGN PATENT DOCUMENTS

CN 1559869 A 1/2005
CN 101185765 A 5/2008
(Continued)

OTHER PUBLICATIONS

"U.S. Appl. No. 16/349,413, Notice of Allowance dated Apr. 23, 2020", 8 pgs.
(Continued)

*Primary Examiner* — Benyam Haile
(74) *Attorney, Agent, or Firm* — Schwegman Lundberg & Woessner, P.A.

(57) ABSTRACT

A system may automatically conduct hygiene cycles for a confined space such an interior space of a box suitable for storing and/or carrying packaged food. The system may include a hygiene device that can be attached to the box to conduct the hygiene cycles. The system may also automatically collect information related to the hygiene cycles and transmit the collected information to a network.

20 Claims, 5 Drawing Sheets

Related U.S. Application Data continuation of application No. 16/349,413, filed as application No. PCT/CN2018/086468 on May 11, 2018, now Pat. No. 10,758,638.

(51) Int. Cl.

| | | |
|---|---|---|
| *A61L 2/22* | (2006.01) | |
| *B08B 9/08* | (2006.01) | |
| *B65D 81/24* | (2006.01) | |
| *A47J 47/14* | (2006.01) | |
| *B08B 9/093* | (2006.01) | |

(52) U.S. Cl.
CPC .............. *B08B 9/093* (2013.01); *B65B 55/02* (2013.01); *B65D 81/24* (2013.01); *A61L 2202/14* (2013.01); *A61L 2202/15* (2013.01); *A61L 2202/16* (2013.01); *A61L 2202/17* (2013.01); *A61L 2202/23* (2013.01)

(58) Field of Classification Search
CPC ......... B65B 55/02; B65B 55/04; B65B 55/12; B67C 7/0066
See application file for complete search history.

(56) References Cited

U.S. PATENT DOCUMENTS

| | | | |
|---|---|---|---|
| 6,550,487 | B1 | 4/2003 | Duckett et al. |
| 7,021,323 | B1 | 4/2006 | Ishikawa et al. |
| 9,595,461 | B2 | 3/2017 | Takahara et al. |
| 10,758,638 | B2 | 9/2020 | Wei et al. |
| 11,285,231 | B2 | 3/2022 | Wei et al. |
| 2002/0003148 | A1 | 1/2002 | Gibson |
| 2002/0134800 | A1 | 9/2002 | Johnson et al. |
| 2004/0118291 | A1 | 6/2004 | Carhuff et al. |
| 2006/0150829 | A1 | 7/2006 | Cheung |
| 2006/0276768 | A1 | 12/2006 | Miller et al. |
| 2008/0152537 | A1 | 6/2008 | Wild et al. |
| 2009/0138107 | A1 | 5/2009 | Ha |
| 2011/0162681 | A1 | 7/2011 | Mulleris |
| 2011/0197464 | A1 | 8/2011 | Chappell et al. |
| 2011/0197921 | A1 | 8/2011 | Rubin et al. |
| 2012/0174795 | A1 | 7/2012 | Uspenski et al. |
| 2012/0241537 | A1 | 9/2012 | Schwei et al. |
| 2012/0251385 | A1 | 10/2012 | Hsieh |
| 2015/0374868 | A1 | 12/2015 | Bruce et al. |
| 2016/0045943 | A1 | 2/2016 | Curran et al. |
| 2016/0107816 | A1 | 4/2016 | Larpenteur et al. |
| 2017/0069199 | A1 | 3/2017 | Magno et al. |
| 2017/0252472 | A1 | 9/2017 | Dang et al. |
| 2017/0286904 | A1 | 10/2017 | Paris, Jr. et al. |
| 2017/0320054 | A1 | 11/2017 | Crum et al. |
| 2018/0078330 | A1 | 3/2018 | Russ |
| 2018/0142394 | A1 | 5/2018 | Debates et al. |
| 2018/0154028 | A1* | 6/2018 | Offutt .................. A61L 2/24 |
| 2018/0184839 | A1* | 7/2018 | Vetterli .................. B08B 9/032 |
| 2018/0236117 | A1 | 8/2018 | Agmont E Silva |
| 2020/0155719 | A1 | 5/2020 | Wei et al. |
| 2020/0261612 | A1 | 8/2020 | Wei et al. |
| 2020/0353117 | A1 | 11/2020 | Wei et al. |

FOREIGN PATENT DOCUMENTS

| | | | |
|---|---|---|---|
| CN | 203279755 U | | 11/2013 |
| CN | 103612828 A | | 3/2014 |
| CN | 103635207 A | | 3/2014 |
| CN | 104144752 A | | 11/2014 |
| CN | 104249896 A | | 12/2014 |
| CN | 104867246 A | * | 8/2015 |
| CN | 104867246 A | | 8/2015 |
| CN | 204854123 U | | 12/2015 |
| CN | 105242657 A | | 1/2016 |
| CN | 105383800 A | | 3/2016 |
| CN | 106575426 A | | 4/2017 |
| CN | 106715274 A | | 5/2017 |
| CN | 206172223 U | | 5/2017 |
| CN | 107187700 A | | 9/2017 |
| CN | 206456776 U | | 9/2017 |
| CN | 107845206 A | | 3/2018 |
| CN | 207197042 U | | 4/2018 |
| CN | 207258372 A | | 4/2018 |
| CN | 207258372 U | | 4/2018 |
| CN | 110720116 A | | 1/2020 |
| CN | 110785359 A | | 2/2020 |
| DE | 19958290 A1 | | 6/2000 |
| FR | 2934991 A1 | | 2/2010 |
| GB | 2123110 A | | 1/1984 |
| JP | H08192125 A | | 7/1996 |
| JP | 2001315721 A | | 11/2001 |
| JP | 2016141427 A | | 8/2016 |
| KR | 100838949 B1 | | 6/2008 |
| KR | 20090041003 A | | 4/2009 |
| KR | 20210005171 A | | 1/2021 |
| WO | WO-2016/113235 A1 | | 7/2016 |
| WO | WO-2019/213933 A1 | | 11/2019 |
| WO | WO-2019/214191 A1 | | 11/2019 |
| WO | WO-2019/214310 A1 | | 11/2019 |

OTHER PUBLICATIONS

"U.S. Appl. No. 16/349,454, Final Office Action dated Dec. 20, 2021", 12 pgs.

"U.S. Appl. No. 16/349,454, Non-Final Office Action dated Mar. 23, 2022", 13 pgs.

"U.S. Appl. No. 16/349,454, Non-Final Office Action dated Jun. 9, 2021", 12 pgs.

"U.S. Appl. No. 16/349,454, Response filed Sep. 9, 2021 to Non-Final Office Action dated Jun. 9, 2021", 12 pgs.

"U.S. Appl. No. 16/349,454, Advisory Action dated Feb. 22, 2022", 3 pgs.

"U.S. Appl. No. 16/349,454, Final Office Action dated Sep. 23, 2022", 15 pgs.

"U.S. Appl. No. 16/349,454, Response filed Feb. 9, 2022 to Final Office Action dated Dec. 20, 2021", 11 pgs.

"U.S. Appl. No. 16/349,454, Response filed Jun. 23, 2022 to Non-Final Office Action dated Mar. 23, 2022", 11 pgs.

"U.S. Appl. No. 16/941,285, Corrected Notice of Allowability dated Feb. 18, 2022", 2 pgs.

"U.S. Appl. No. 16/941,285, Non-Final Office Action dated Jul. 14, 2021", 13 pgs.

"U.S. Appl. No. 16/941,285, Notice of Allowance dated Nov. 23, 2021", 8 pgs.

"U.S. Appl. No. 16/941,285, Response filed Oct. 13, 2021 to Non Final Office Action dated Jul. 14, 2021", 9 pgs.

"Chinese Application Serial No. 201880004352.0, Notification to Make Rectification dated Nov. 21, 2019", (w/ English Translation), 2 pgs.

"Chinese Application Serial No. 201880004352.0, Office Action dated Feb. 9, 2022", (w/ English Translation), 23 pages.

"Chinese Application Serial No. 201880004352.0, Office Action dated Aug. 16, 2022", (w/ English Translation), 25 pgs.

"Chinese Application Serial No. 201880004352.0, Response filed Jun. 8, 2022 to Office Action dated Feb. 9, 2022", (w/ English Translation of Claims), 18 pgs.

"Chinese Application Serial No. 201980000626.3, Office Action dated Apr. 22, 2022", (w/ English Translation), 29 pgs.

"Chinese Application Serial No. 201980000626.3, Office Action dated Aug. 8, 2022", (w/ English Translation), 31 pgs.

"Chinese Application Serial No. 201980000626.3, Response filed Jun. 21, 2022 to Office Action dated Apr. 22, 2022", (w/ English Translation of Claims), 23 pgs.

"Chinese Application Serial No. 201980000626.3, Office Action dated Nov. 22, 2021", with English translation, 27 pages.

"Chinese Application Serial No. 201980000626.3, Response Filed Mar. 18, 2022 to Office Action dated Nov. 22, 2021", (w/ English Translation of Claims), 28 pages.

(56) References Cited

OTHER PUBLICATIONS

"European Application Serial No. 19798975.9, Response filed Jun. 25, 2021 to Communication pursuant to Rules 161(2) and 162 EPC", 13 pgs.
"European Application Serial No. 19798975.9, Extended European Search Report dated Mar. 7, 2022", 10 pgs.
"European Application Serial No. 19798975.9, Response filed Sep. 13, 2022 to Extended European Search Report dated Mar. 7, 2022", 15 pgs.
"Indian Application Serial No. 202017051624, First Examination Report dated Jan. 21, 2022", 6 pgs.
"Indian Application Serial No. 202017051624, Response filed Jul. 21, 2022 to First Examination Report dated Jan. 21, 2022", 218 pgs.
"Indonesian Application Serial No. P00202008822, Office Action dated Oct. 3, 2022", (w/ English Translation), 4 pgs.
"International Application Serial No. PCT/CN2018/086468, International Search Report dated Feb. 11, 2019", 5 pgs.
"International Application Serial No. PCT/CN2018/086468, Written Opinion dated Feb. 11, 2019", 4 pgs.
"International Application Serial No. PCT/CN2018/114274, International Search Report dated Feb. 15, 2019", 4 pgs.
"International Application Serial No. PCT/CN2018/114274, Written Opinion dated Feb. 15, 2019", 4 pgs.
"International Application Serial No. PCT/CN2019/075440, International Search Report dated Apr. 25, 2019", 4 pgs.
"International Application Serial No. PCT/CN2019/075440, Written Opinion dated Apr. 25, 2019", 4 pgs.
"Korean Application Serial No. 10-2020-7034033, Notice of Preliminary Rejection dated Jun. 17, 2022", (w/ English Translation), 17 pgs.
"Machine Translation of CN104867246A", (2015), 7 pgs.
"Machine Translation of CN207258372U", (2018), 7 pgs.
"Singaporean Application Serial No. 11202011142Y, Written Opinion dated Apr. 1, 2022", 4 pgs.
Zuo, Chunkuan, et al., "Marine Power Plant", (Jun. 30, 2012), 7pgs.
U.S. Appl. No. 16/349,413 U.S. Pat. No. 10,758,638, filed May 13, 2019, Hygiene System for a Portable Packaged Food Container.
U.S. Appl. No. 16/941,285 U.S. Pat. No. 11,285,231, filed Jul. 28, 2020, Hygiene System for a Portable Packaged Food Container.
U.S. Appl. No. 16/349,454, filed May 13, 2019, Method for Controlling Hygiene of a Portable Packaged Food Container (as amended).
"U.S. Appl. No. 16/349,454, Non Final Office Action dated Feb. 16, 2023", 15 pgs.
"U.S. Appl. No. 16/349,454, Response filed May 16, 2023 to Non Final Office Action dated Feb. 16, 2023", 10 pgs.
"U.S. Appl. No. 16/349,454, Response filed Nov. 22, 2022 to Final Office Action dated Sep. 23, 2022", 14 pgs.
"Chinese Application Serial No. 201880004352.0, Notification to Grant dated Dec. 5, 2022", (w/ English Translation), 9 pgs.
"Chinese Application Serial No. 201980000626.3, Decision of Rejection dated Dec. 9, 2022", (w/ English Translation), 16 pgs.
"Chinese Application Serial No. 201980000626.3, Response filed Oct. 21, 2022 to Office Action dated Nov. 22, 2021", (w/ English Translation), 7 pgs.
"European Application Serial No. 19798975.9, Communication Pursuant to Article 94(3) EPC dated Jun. 28, 2023", 6 pgs.
"Korean Application Serial No. 10-2020-7034033, Notice of Preliminary Rejection dated Nov. 10, 2022", (w/ English Translation), 5 pgs.
"Korean Application Serial No. 10-2020-7034033, Notice to Grant dated Mar. 22, 2023", (w/ English Translation), 4 pgs.
"Korean Application Serial No. 10-2020-7034033, Response filed Dec. 26, 2022 to Notice of Preliminary Rejection dated Nov. 10, 2022", (w/ English Translation of Claims), 9 pgs.
Liu, C. J., et al., "Development and Application of a "Foreign Device" Module in IMS of the Sterilization and Supply Center", (Abstract), China Medical Devices, No. 2, (Feb. 25, 2015), 1 pg.

\* cited by examiner

HYGIENE SYSTEM FOR A PORTABLE PACKAGED FOOD CONTAINER

CROSS-REFERENCE TO RELATED APPLICATION

This application is a continuation of U.S. patent application Ser. No. 16/941,285, filed Jul. 28, 2020, now issued as U.S. Pat. No. 11,285,231, which is a continuation of U.S. patent application Ser. No. 16/349,413, filed May 13, 2019, now issued as U.S. Pat. No. 10,758,638, which is a U.S. National Stage Filing under 35 U.S.C. 371 from International Application No. PCT/CN2018/086468, filed on May 11, 2018, which applications are incorporated herein by reference in their entirety.

TECHNICAL FIELD

This document relates generally to device hygiene and more particularly to a method and apparatus for conducting automatic cleaning and/or sanitization cycles for a confined space such as interior of a box for containing packaged food.

BACKGROUND

Small and confined spaces, such as the interior of a food delivery box, are difficult to clean and/or sanitize. For example, boxes used to deliver ready-to-eat foods, such as ordered by a customer from a restaurant, need periodic cleaning and sanitization to ensure food hygiene. This may be done by manually spraying a chemical agent onto surfaces of each delivery box. Quality and thoroughness of such manual cleaning and/or sanitization depends on the person performing the procedure, and are inconsistent because, for example, there is no mechanism ensuring that the entire surfaces are covered and/or in a substantially uniform fashion. A two-step cleaning and sanitizing procedure makes each cycle even more complicated and less consistent. Additionally, a manual operation does not provide an objective record showing that a hygiene procedure is routinely followed.

SUMMARY

A system may automatically conduct hygiene cycles for a confined space such an interior space of a box suitable for storing and/or carrying packaged food. The system may include a hygiene device that can be attached to the box to conduct the hygiene cycles. The system may also automatically collect information related to the hygiene cycles and transmit the collected information to a network.

An example of a system for cleaning and sanitizing a box configured to be carried by a user may include a hygiene device. The hygiene device may be configured to be attached to the box, and may include an agent container configured to contain a hygiene agent, a spray nozzle configured to be inserted into the box (or otherwise placed in the box to perform its function), a pump in fluid communication with the agent container and in fluid communication with the spray nozzle, and a control circuit. The pump may be configured to pump the hygiene agent through the spray nozzle to produce a mist of the hygiene agent in the box. The control circuit may be configured to control hygiene cycles and may include a communication circuit configured to transmit and receive information, a hygiene cycle management circuit configured to initiate each cycle of the hygiene cycles, and a monitoring circuit configured to record information related to performance of each cycle of the hygiene cycles and to transmit the recorded information out of the hygiene device through the communication circuit.

An example of a method for cleaning and sanitizing a box configured to be carried by a user is also provided. The method may include verifying emptiness of the box, starting an automatic hygiene cycle using a battery-powered portable hygiene device attached to the box, recording information related to performance of the hygiene cycle, and transmitting the recorded information to an analysis center for analysis and monitoring of hygiene status of the box.

This summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
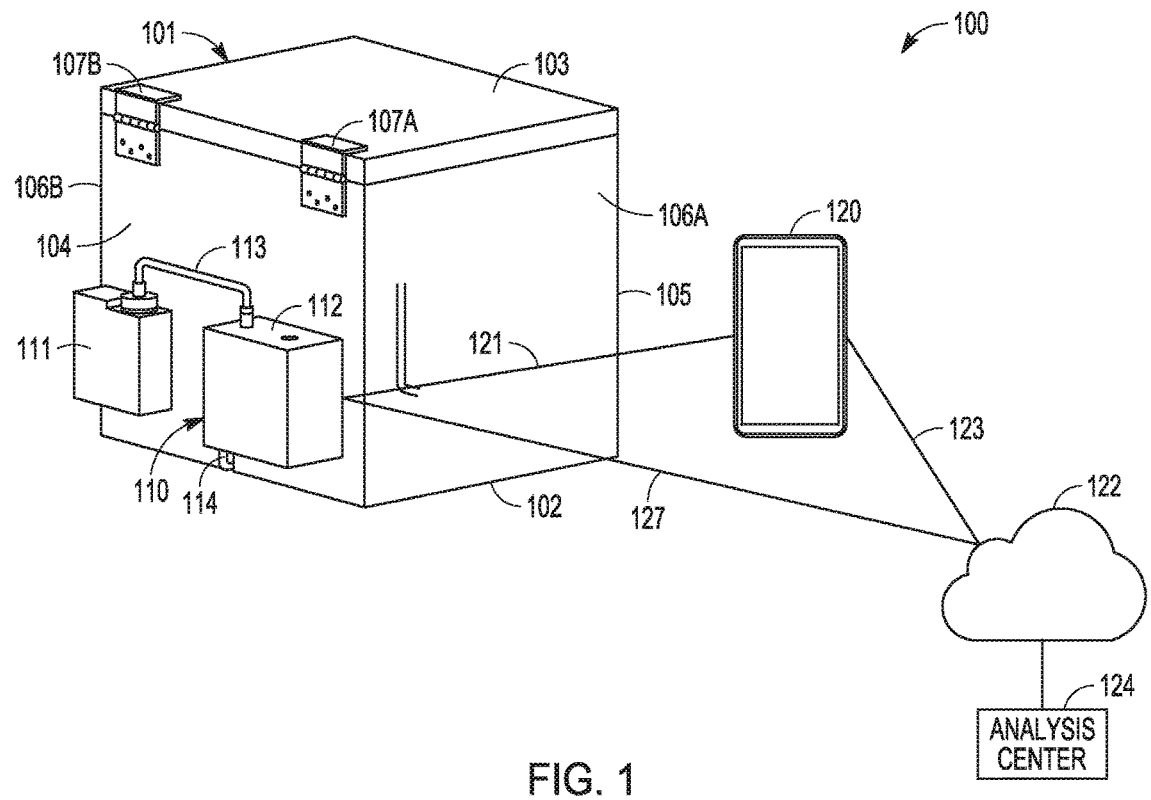
FIG. 1 is a block diagram illustrating an embodiment of a system for cleaning and sanitizing a box.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present invention is defined by the appended claims, along with the full scope of legal equivalents to which such claims are entitled.

This document discusses, among other things, a system for automatically conducting hygiene cycles for a confined space and automatically logging the hygiene cycles. The system can be constructed as a portable clean-in-place ("CIP") system. The hygiene cycle log can include various information collected by the system and can be transmitted to an analysis center through a telecommunication network.

In this document, "hygiene" can include cleaning, sanitization, or cleaning and sanitization (C&S). For example, a "hygiene agent" can include a cleaning agent, a sanitization agent, or a cleaning and sanitization (C&S) agent; a "hygiene cycle" can include a cleaning cycle, a sanitization cycle, or a cleaning and sanitization (C&S) cycle; and a "hygiene procedure" can include a cleaning procedure, a sanitization procedure, or a cleaning and sanitization (C&S) procedure.

An example of the confined space includes the confined space in a closed box for carrying or storing packaged ready-to-eat foods. An example of such a box includes a food delivery box for carrying cooked foods from a kitchen to a dinning place in a place remote from the kitchen. A hygiene procedure for such a box may be established to ensure food safety (e.g., according to pertinent regulatory requirements). When the procedure is carried out manually, compliance is difficult to ensure, and no objective evidence of compliance is recorded.

The present system provides an intelligent system that can spray a hygiene agent onto surfaces of a confined space with a substantially uniform distribution under automatic control for conducting hygiene cycles periodically or according to other specified schedule and/or criteria. In some embodiments, a 2-in-1 hygiene agent (also referred to as a C&S agent) combines cleaning and sanitation into an efficient single step. The present system also collects hygiene cycle information automatically and transmits the collected information to one or more designated receiving locations for analysis and monitoring.

Existing hygiene systems that are intended for large spaces and need much power to operate, plenty of water to flush, and compress air to dry are not suitable for small spaces such as the food delivery box, which can be small enough, for example, to be carried by hand and/or by an electric moped or motorcycle. The present system can be battery-powered and portable, such as a system that can be easily attached to the food delivery box to perform controlled spray of the hygiene agent onto interior surfaces of the food delivery box when it is empty. In one embodiment, the present system uses a single spray nozzle configured to function with a diaphragm pump to spray the hygiene agent with nebulization to ensure that the hygiene agent covers all surfaces of a confined space, such as the cavity of a rectangular box having six planar surfaces.

In various embodiments, the present system can include a control system that receives a command and initiates a hygiene cycle in response to the command. The command can be received by the system from a remote device via a communication link. In response to the hygiene cycle being initiated, an electronic circuit of the present system generates a signal to start the diaphragm pump to spray, resulting in a substantially uniform distribution of the hygiene agent on all the surfaces of the confine space. The electronic circuit can control automatic conduction of the hygiene cycle, record time of the hygiene cycle and/or other hygiene cycle information, and send the recorded information including the time to the analysis center.

In various embodiments, the hygiene agent can include one or more chemical substances in liquid form. An example of the hygiene agent includes a cleaning agent, a sanitization agent, or a 2-in-1 C&S agent selected such that when being sprayed into a confined space using the present system, the quantity of the agent distributed on surfaces of the confined space can produce a result that satisfies pertinent regulatory requirements for cleaning and sanitizing efficacy. This quantity of agent distribution can be achieved by configuring the spray nozzle and diaphragm pump to provide for chemical nebulization and determining a duration of spraying for each hygiene cycle.

While a hygiene system for the food delivery box is specifically discussed in this document as an example, the present subject matter is not limited to such an application, but can be used to apply liquid and/or gas into any confined space, for purposes including but not limited to cleaning and sanitizing the confined space. Some examples of devices having cavities that can be cleaned and sanitized by applying the present subject matter include like refrigerators, microwave ovens, food containers in any shape, containers of non-food items that needs cleaning and sanitization, storage and/or delivery boxes (not limited to food storage and/or delivery), and wash machines. Additionally, the present subject matter is not limited to spraying liquid hygiene agents, but can also be used to spray various other liquid or gas such as pest control agents.

FIG. 1 is a block diagram illustrating an embodiment of a system 100 for cleaning and sanitizing a box 101. Box 101 can include any container having a cavity that needs to be cleaned and sanitized. In the illustrated embodiment, box 101 is a rectangular box with a flat, rectangular bottom 102 (only edges shown in FIG. 1), a lid (or cover) 103, and four sides. The four sides include a front side 105 (only an edge shown in FIG. 1), a rear side 104, and 2 lateral sides 106A and 106B (only an edge shown in FIG. 1) each coupled between front side 105 and rear side 104. Lid 103 is connected to rear side 104 with hinges 107A and 107B. In various embodiments, lid 103 is connected to rear side 104 with one or more hinges. Box 101 can be securely closed using a locking mechanism (not shown) that locks lid 103 in a closed position. When lid 103 is in the closed position (as shown in FIG. 1), a confined space is formed by interior surfaces of box 101, including interior surfaces of bottom 102, front side 105, rear side 104, lateral sides 106A and 106B, and lid 103. This confined space can be cleaned and sanitized by using the present subject matter.

An example of box 101 is a food storage and/or delivery box such as a portable food delivery box. In various embodiments, box 101 as a food delivery box can be carried by hand and/or attached onto a vehicle such as a bicycle, a moped, or a motorcycle. For example, the food delivery box can be attached onto the vehicle with rear side 104 facing the forward-moving direction of the vehicle. In various embodiments, box 101 is used to contain packaged foods without direct contact between the foods and the interior surfaces of the box. When being used properly, no solid or liquid food waste or stain should remain on the interior surfaces of box 101 so that no rinse is needed for cleaning. Manual cleaning may be needed in case of an accidental food spill.

System 100 can be an automatic hygiene system that includes a hygiene device 110, a user interface device 120, and an analysis center 124 that can communicate with user interface device 120 through a network 122. Hygiene device 110 can be attached to box 101. In some embodiments, hygiene device 110 is configured to be detachably attached to box 101. In the illustrated embodiment, hygiene device 110 includes a container unit 111 to contain a hygiene agent, a controller unit 112 to control delivery of the hygiene agent to a spray nozzle (not shown in FIG. 1), tubing 113 between container unit 111 and controller unit 112, and tubing 114 between controller unit 112 and the spray nozzle. It should be understood that arrangement of system components (e.g., how the components of hygiene device 110 are physically arranged, housed, and attached to box 101) as shown in FIG. 1 and other figures in this documents are each illustrated by way of example and not by way of restriction. Such arrangement can be determined based on design considerations such as a specific shape and size of box 101 and where box 101 is to be placed and/or how box 101 is to be transported.

User interface device 120 is capable of transmitting and receiving information via one or more wireless communication links, such that it can present instructions to a user of box 101 and receive confirmation and/or commands from the user. In this document, a "user" includes a person who uses system 100 to clean and sanitize box 101. When box 101 is a portable food delivery box, the user may be a delivery person (also referred to as "driver", "rider", etc) who is assigned the task of cleaning and/or sanitizing the box. Such a delivery person can include any person carrying the box by hand and/or using any vehicle. User interface device 120 can communicate with hygiene device 110 via a wireless communication link 121 (e.g., using Bluetooth technology), and can communicate with network 122 via another wireless communication link 123 (e.g., the Internet through Wi-Fi, or a cellular network). In various embodiments, user interface device 120 can present the instructions to the user using a touchscreen and/or a speaker, and can receive the confirmation and/or commands from the user using the touchscreen and/or a microphone. For example, communicating with the user using the speaker and the microphone (e.g., a headphone set with a microphone) allows for hand-free operation at least to some extent. In various embodiments, user interface device 120 includes a mobile device such as a cellphone or a tablet computer.

Analysis center 124 can represent one or more data analysis and/or monitoring facilities that communicate with many boxes of a business organization, such as all the food delivery boxes of a food delivery company, or a subset such as all the food delivery boxes within a region or a subsidiary of the food delivery company. This allows the organization to efficiently and effectively manage the cleaning and/or sanitization of the boxes, such as for ensuring food safety and/or meeting regulatory requirements.

Network 122 can represent any network including, but not limited to, a telecommunication network, a local network, the Internet, or the Internet of Things (IoT). In various embodiments, network 122 includes the IoT with user interface device 120 and analysis center 124 each being part of it. In some embodiments, hygiene device 110 can communicate with network 122 directly (without user interface device 120) via another wireless communication link 127 (e.g., Wi-Fi or cellular network). This allows for communication between analysis center 124 or other operation control or management centers and hygiene device 110 directly when, for example, communication with user interface device 120 via links 121 and/or 123 is unavailable for any reason. In some embodiments, hygiene device 110 can be configured to be part of the IoT, and network 122 can represent the IoT, with hygiene device 110, user interface device 120, and analysis center 124 each being part of it.

Figure 2:
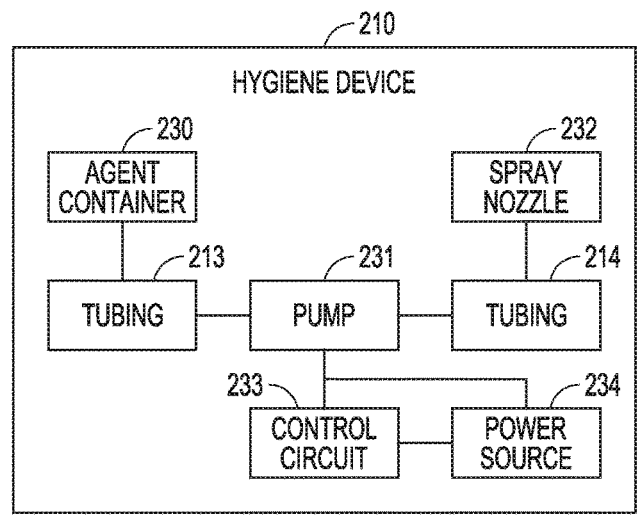
FIG. 2 is a block diagram illustrating an embodiment of a hygiene device of the system of FIG. 1.

FIG. 2 is a block diagram illustrating an embodiment of a hygiene device 210, which represents an example of components of hygiene device 110. Hygiene device 210 can include an agent container 230, tubing 213, a pump 231, tubing 214, a spray nozzle 232, a control circuit 233, and a power source 234.

Agent container 230 contains the hygiene agent. Depending on the purpose of conducting hygiene cycles, the hygiene agent can be a liquid chemical agent that has cleaning effects only, sanitization effects only, or both cleaning and sanitization effects. A hygiene agent that has both cleaning and sanitization effects can be referred to as a 2-in-1 hygiene agent or 2-in-1 C&S agent. Using such a 2-in-1 hygiene agent allow each C&S hygiene cycle to be performed with a single spraying action. In various embodiments, agent container 230 includes a refillable or disposable bottle suitable for containing the hygiene agent. Pump 231 can receive the hygiene agent from agent container 230 through tubing 213 and deliver the hygiene agent to spray nozzle 232 through tubing 214. An example of pump 231 includes a diaphragm pump. Spray nozzle 232 works with pump 213 to produce a mist of the hygiene agent in a confined space of a box such as box 101 to result in substantially uniform distribution of the hygiene agent on the interior surfaces of the box. In one embodiment as a specific example discussed in this document, spray nozzle 232 includes a single nozzle incorporated into the bottom of the box, such as by inserting into the box through a hole in a geometric center of the bottom of the box. In various embodiments, spray nozzle 232 can include one or more spray nozzles incorporated into the bottom, the lid, and/or each side of the four sides of the box to produce a mist of the hygiene agent in the box to result in substantially uniform distribution of the hygiene agent on the interior surfaces of the box. Control circuit 233 can include an electronic circuit configured to control conduction of the hygiene cycles. Power source 234 provides power for the operation of hygiene device 210. Power source 234 can include one or more rechargeable and/or non-rechargeable batteries.

In one embodiment, the components of hygiene device 210 are arranged and attached to the box as illustrated in FIG. 1, with container unit 111 including agent container 230, tubing 113 corresponding to tubing 213, controller unit 112 including pump 231, control circuit 233, and power source 234, tubing 114 corresponding to tubing 214, and spray nozzle 232 installed at bottom 102. In various embodiments, the components of hygiene device 210 can be arranged and coupled to the box in any way that ensures portability of the box.

Figure 3:
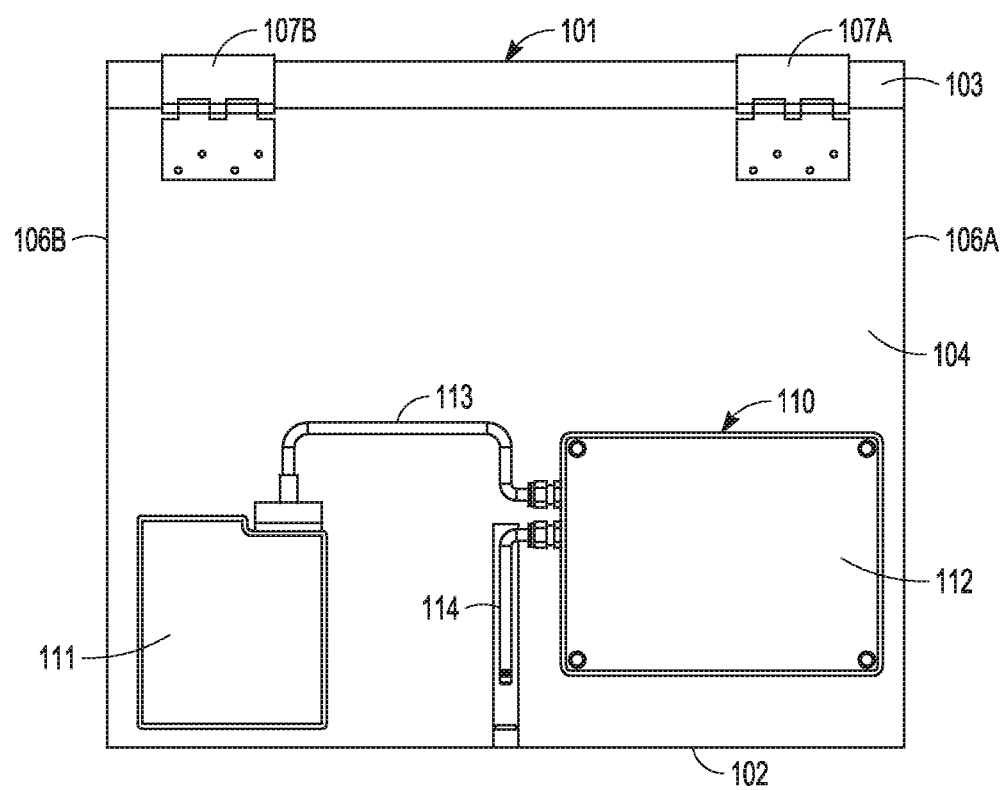
FIG. 3 is a diagram illustrating of an embodiment of portions of the hygiene device as seen from a rear view of the box.

FIG. 3 is a diagram illustrating of an embodiment of portions of hygiene device 110 as seen from a rear view of box 101. Components of box 101 that are shown in FIG. 3 include bottom 102 (only an edge shown), lid 103 (only an edge shown), lateral sides 106A (only an edge shown) and 106B (only an edge shown), and rear side 104. Components of hygiene device 110 that are shown in FIG. 3 include container unit 111, tubing 113, controller unit 112, and tubing 114.

Figure 4:
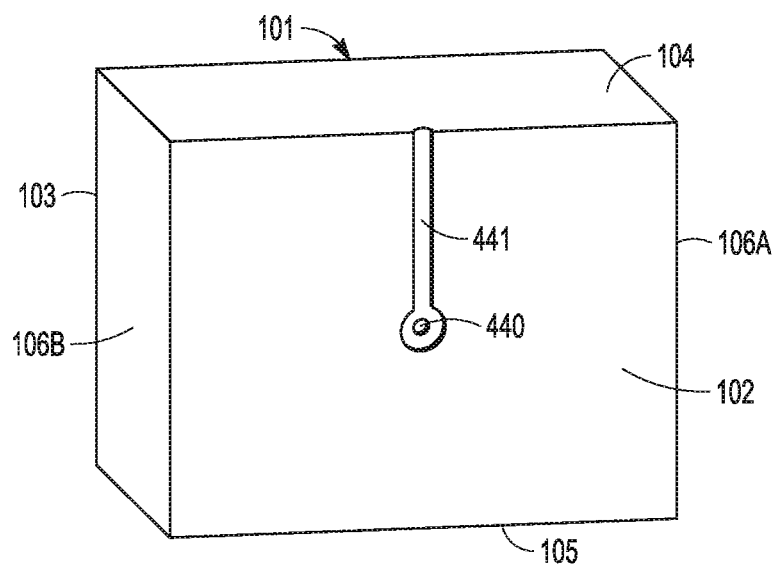
FIG. 4 is a diagram illustrating of an embodiment of a bottom of the box configured to accommodate a spray nozzle of the hygiene device.

FIG. 4 is a diagram illustrating of an embodiment of bottom 102 of box 101 configured to accommodate a spray nozzle. Components of box 101 that are shown in FIG. 4 include bottom 102, lid 103 (only two edges shown), rear side 104, front side 105 (only two edges shown), and lateral sides 106A (only two edges shown) and 106B. Bottom 102 includes a hole 440 sized and shaped to allow placement of the spray nozzle such as spray nozzle 232. Bottom 102 also includes a groove 441 to accommodate a portion of tubing 114 that is connected to the spray nozzle.

Figure 5:
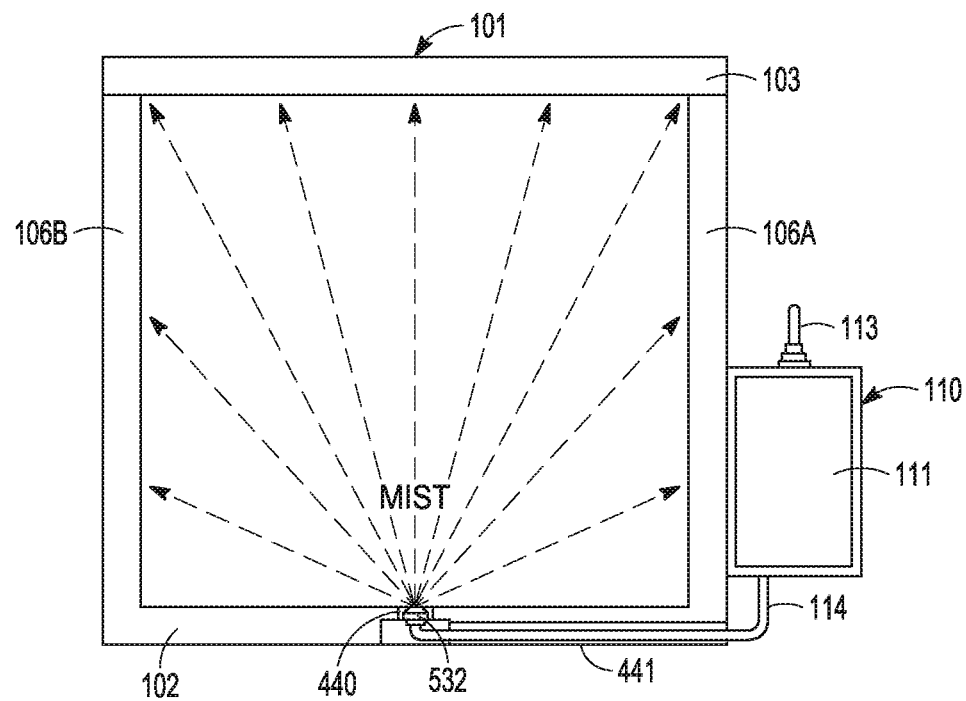
FIG. 5 is a diagram illustrating of an embodiment of portions of the hygiene device as seen on a cross-sectional view of the box.

FIG. 5 is a diagram illustrating of an embodiment of portions of hygiene device 110 as seen on a cross-sectional view of box 101. Components of box 101 that are shown in FIG. 5 include bottom 102 with hole 440 and groove 441, lid 103, and lateral sides 106A and 106B. Components of hygiene device 110 that are shown in FIG. 3 include container unit 111, tubing 113, tubing 114, and a spray nozzle 532 representing an example of spray nozzle 232 and shown as producing a mist distributing the hygiene agent onto the interior surfaces of box 101.

Figure 6:
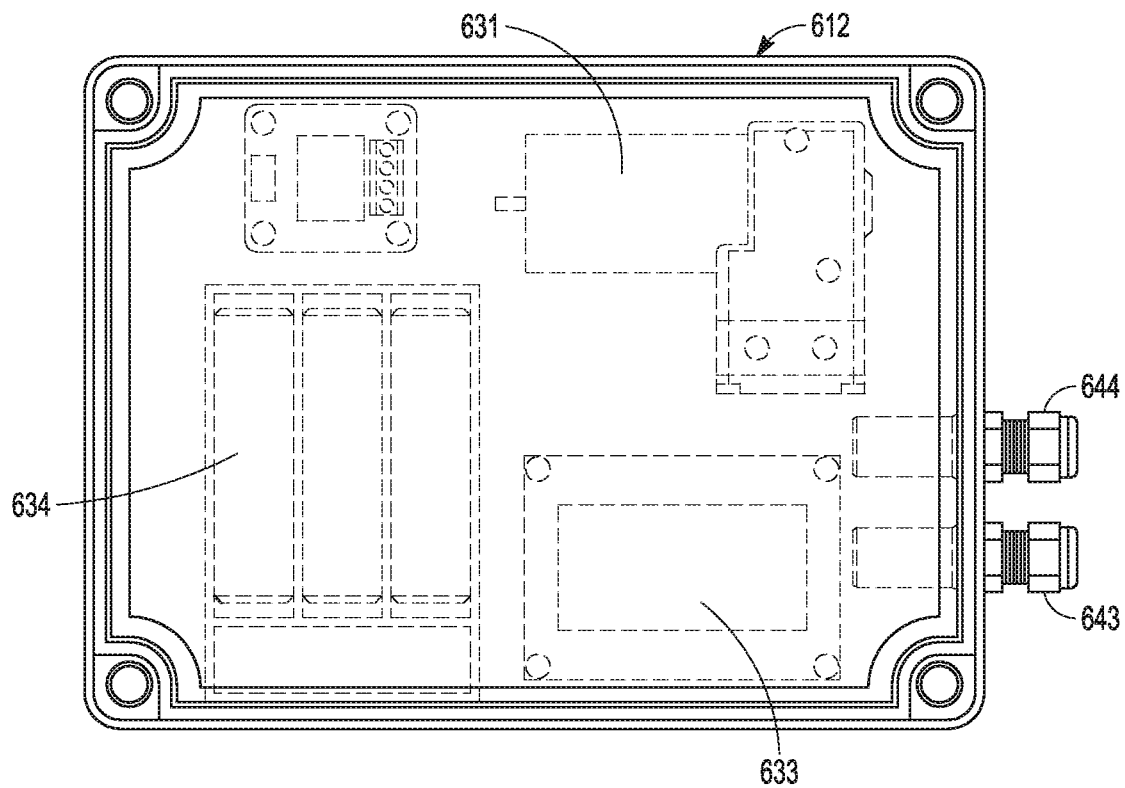
FIG. 6 is a diagram illustrating of an embodiment of a controller unit of the hygiene device.
Figure 7:
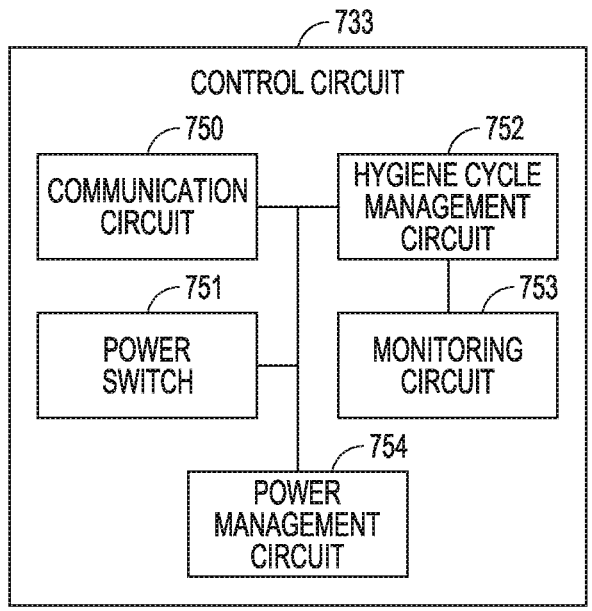
FIG. 7 is a block diagram illustrating an embodiment of a control circuit of the hygiene device.

FIG. 6 is a diagram illustrating of an embodiment of a controller unit 612, which represent an example of controller unit 112. Controller unit 612 as illustrated in FIG. 6 shows an example of placement of its major components including a pump 631 (representing an example of pump 231), a control circuit 633 (representing an example of control circuit 233), a battery pack 634 (representing an example of power source 234), a tubing connector 643 configured to connect to tubing 113, and a tubing connector 644 configured to connect to tubing 114, FIG. 7 is a block diagram illustrating an embodiment of a control circuit 733, which represent an example of control circuit 233. Control circuit 733 can include a communication circuit 750, a power switch 751, a hygiene cycle management circuit 752, a monitoring circuit 753, and a power management circuit 754.

Communication circuit 750 provides for communication between user interface device 120 and hygiene device 110 via wireless communication link 121, such as using Bluetooth technology. In various embodiments, communication circuit 750 transmits data collected by hygiene device 110 to user interface device 120, receives commands controlling operation of hygiene device 110 from user interface device 120, and transmits signals indicative of operational status of hygiene device 110 to user interface device 120. User interface device 120 can function as a relay device for communications between hygiene device 110 and analysis center 124 (or any other operation control or management center) through network 122. In some embodiments, communication circuit 750 also provides for communication between network 122 and hygiene device 110 via wireless communication link 123, such as using Wi-Fi or a cellular network. Communication circuit 750 can transmit data collected by hygiene device 110 to analysis center 124, receive commands control ling operation of hygiene device 110 from analysis center 124, and transmit signals indicative of operational status of hygiene device 110 to analysis center 124, through network 122 without using user interface device 120 as a relay device.

Power switch 751 can include any switch suitable for turning electric power on and off. This allows the user to turn hygiene device 110 on and off Hygiene cycle management circuit 752 can initiate and control a hygiene cycle according to programmed schedule, criteria, and/or user command. In various embodiments, hygiene cycle management circuit 752 can be configured to initiate a hygiene cycle periodically (e.g., every 4 hours) or according to a specified (e.g. programmable) schedule (e.g., at 10:30 am, 2:00 pm, 5:00 pm, and 8:00 pm). Hygiene cycle management circuit 752 can also be configured to initiate a hygiene cycle in response to a user command (e.g., over-riding the specified schedule). The user command can include a command transmitted from user interface device 120 and received by communication circuit 750. In various embodiments, hygiene cycle management circuit 752 can confirm that box 101 is empty and that lid 103 is closed, and can start spraying the hygiene agent upon the confirmation. For example, hygiene cycle management circuit 752 can transmit a confirmation request signal thought communication circuit 750 to user interface device 120, and receive a confirmation response signal confirming that box 101 is empty and that lid 103 is closed from user interface device 120. User interface device 120 can present the confirmation request signal as an audial and/or visual message to the user, and receive the response from the user as the confirmation response signal. The confirmation response signal can act as a command for starting the spraying of the hygiene agent, i.e., hygiene cycle management circuit 752 can start spraying the hygiene agent upon receiving the confirmation response signal. In various embodiments, hygiene cycle management circuit 752 can also control the performance of the hygiene cycle following its initiation, including controlling the pumping of the hygiene agent during the hygiene cycle. For example, hygiene cycle management circuit 752 can control the duration of the pumping of the hygiene agent by timing the pumping and ending the pumping when a specified time interval expires.

Monitoring circuit 753 can record information indicative of performance of each hygiene cycle and transmit the recorded information to network 122 (in other words, "upload data to the cloud"). In various embodiments, the recorded information can include information identifying box 101 (e.g., a serial number), the user (e.g., the delivery person using the box), time of the hygiene cycle (e.g., starting, ending, and/or actual spraying times), and/or location where the hygiene cycle is conducted. In various embodiments, the recorded information is transmitted to network 122 such that analysis center 124 can analyze the recorded information and send instructions and/or warnings to user interface device 120 based on an outcome of the analysis (e.g., to ensure compliance of hygiene procedures), receive recorded information from all the delivery boxes equipped with the hygiene devices (e.g., company-wide, region-wide, or nationwide) on a regular basis, report performance (e.g., statistical data) of the hygiene cycles for the delivery boxes to management (e.g., a designated person or team) periodically (e.g., monthly), and/or send instructions to each user and/or each team leader managing a plurality of users from the management. In various embodiments, monitoring circuit 753 can also monitor the status of the hygiene cycle and notify the user by transmitting information indicative the status of the hygiene cycle to user interface device 120. When the transmitted information indicates that the hygiene cycle is completed, user interface device 120 can present an instruction for the user to open lid 103 to allow natural drying or to use paper towel to wipe the interior surfaces of box 101 upon completion of the hygiene cycle (e.g., for compliance with regulatory requirement) and/or to perform certain other tasks in compliance with pertinent regulatory requirements.

Power management circuit 754 can manage the operation of power source 234 and control distribution of electric power to various components of hygiene device 110 that require the electric power to function (e.g., pump 231 and control circuit 233 or 733). When power source 234 includes one or more batteries, power management circuit 754 can monitor the remaining level of the one or more batteries and produce a battery level alter signal in response to the level dropping under a battery level threshold. Power management circuit 754 can transmit this battery level alert signal though communication circuit 750 to user interface circuit 120 to remind the user to replace or recharge the one or more batteries of power source 234. In one embodiment, the user interface device 120 reminds the user to replace or recharge the battery periodically (e.g., weekly).

In some embodiments, control circuit 733 is configured to determine the location of hygiene device 110 using a positioning system such as the global positioning system (GPS) or location based services (LBS). This allows for tracking of hygiene device 110 and use of its location tracks to determine whether a hygiene cycle should be conducted. Hygiene cycle management circuit 752 can use the location of hygiene device 110 as one of the criteria to initiate the hygiene cycle. For example, when box 101 is due for a scheduled hygiene cycle, hygiene cycle management circuit 752 can track the location of the attached hygiene device 110 and initiate the hygiene cycle after box 101 with hygiene device 110 returns after a food delivery to a facility while the delivered foods are prepared. The information about the hygiene cycle recorded and transmitted by monitoring circuit 753 can also include the location where the hygiene cycle is conducted. Control circuit 733 and/or analysis center 124 can analyze the recorded information to determine whether the hygiene procedure is complied, for example, by determining the number of food deliveries (as monitored by tracking locations of hygiene device 110) between two hygiene cycles. Control circuit 733 can also send information indicating location of hygiene device 110 to network 122 to allow for tracking of hygiene device 110 by analysis center 124 and/or other operation control or management centers for various other purposes. For example, the location of hygiene device 110 can be tracked for recording and analyzing routes of food delivery to improve timing or efficiency, or to monitor whether hygiene device 110 is deployed in compliance of the hygiene procedure.

Figure 8:
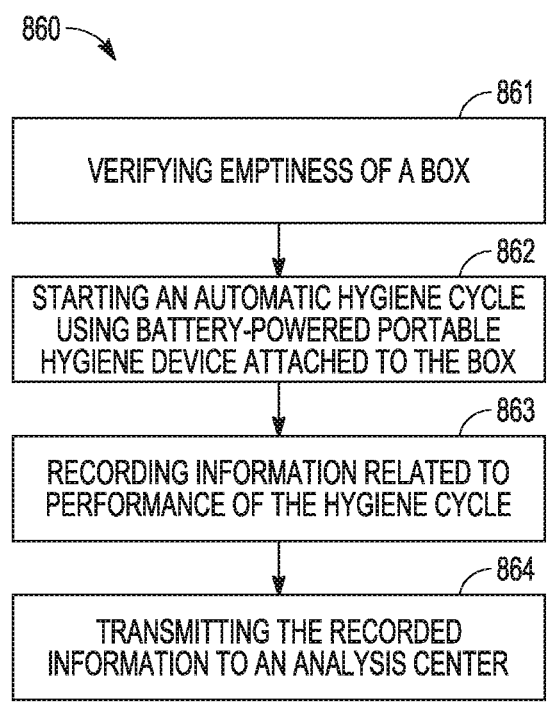
FIG. 8 is a flow chart illustrating an embodiment of a method for cleaning and sanitizing a box.

FIG. 8 is a flow chart illustrating an embodiment of a method 860 for cleaning and sanitizing a box, such as box 101. In one embodiment, system 100 is configured for performing method 860. In one embodiment, a user interface device such as user interface device 120 is configured to control the performance of method 860. For example, the user interface device can include a cellphone, and an application is installed on the cellphone for controlling the performance of method 860. The application can present reminder and instructions to the user before, after, and during each hygiene cycle.

At 861, emptiness of the box is verified. If the box is not empty (e.g., food is contained in the box), the contents must be removed before a hygiene cycle can be started. If the box is not empty because it is dirty (e.g., resulting from food spill), the box can be manually cleaned (e.g., using a paper towel to wipe out solid or liquid food spills). Emptiness of the box can then be verified.

At 862, an automatic hygiene cycle is started in response to a command indicating the verification that the box is empty. The hygiene cycle can be automatically conducted using a battery-powered portable hygiene device attached to the box, such as hygiene device 110.

At 863, information related to performance of the hygiene cycle is recorded by the battery-powered portable hygiene device. Such information indicates whether a hygiene procedure is complied, for example for ensuring food safety and/or meeting regulatory requirements.

At 864, the recorded information is transmitted to an analysis center, such as by uploading data representing the recorded information to a network. This concludes the hygiene cycle. In various embodiments, the transmission of the recorded information can be triggered by end of each hygiene cycle, on a periodic basis, by a data transmission command transmitted from the user interface device, and/or by a detection of failure in complying with the hygiene procedure. The recorded information can be transmitted to the analysis center from the battery-powered portable hygiene device directly and/or via the user interface device.

In various embodiments, upon completion of the hygiene cycle, interior surfaces of the box are to be dried by the user. This can be done by opening the lid of the box to allow natural air dry. Alternatively, this can be done by opening the lid of the box and wiping all the interior surfaces of the box (e.g., using a paper towel), such as when time or weather does not allow for air dry. When the box is used for food delivery, no liquid (i.e., the hygiene agent) should remain in the box when loading packaged food for the next food delivery.

In various embodiments, exterior of the box is also to be cleaned periodically. Such cleaning can be performed manually.

In various embodiments in which the container of the hygiene agent is refillable, the container is to be cleaned before each refill or after a specified number of refills. Other parts of the hygiene device (e.g., the nozzle and/or the tubing) are also to be cleaned periodically or as needed.

Figure 9:
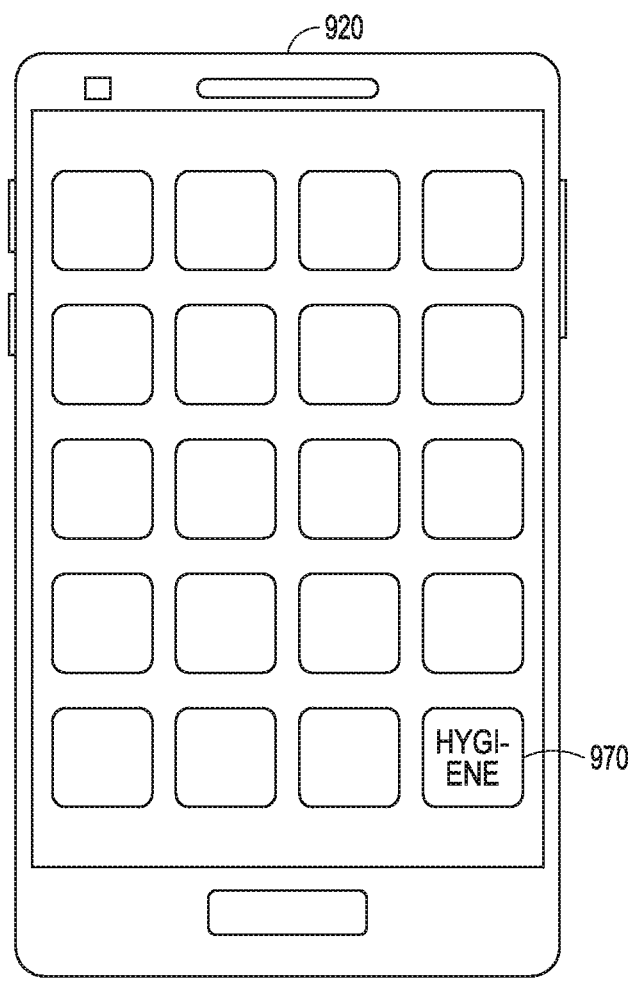
FIG. 9 is a diagram illustrating an embodiment of a user interface device of the system of FIG. 1.

FIG. 9 is a diagram illustrating an embodiment of a user interface device 920, which can represent an embodiment of user interface device 120. In the illustrated embodiment, user interface device 920 is a cellphone on which a hygiene application 970 is installed. The cellphone is to be carried by each delivery person (or another person) responsible for compliance with the hygiene procedure.

In various embodiments, functions performed by application 970 through cellphone 920 can include those selected from the following examples:
  presenting food safety tips for home delivery of cooked food;
  displaying a training video on a hygiene procedure for home delivery of cooked food;
  reminding the user that a hygiene cycle is starting (with an audial and/or visual message);
  instructing the user to check whether the box is empty;
  receiving confirmation from the user that the box is empty;
  triggering spray of the hygiene agent during each hygiene cycle;
  recording information related to each hygiene cycle;
  sending the recorded information to the network (uploading data representative of the recorded information to the analysis center through the network as triggered by end of each hygiene cycle, on a periodic basis, by a transmission command from the user, and/or by a detection of failure in complying with a hygiene procedure;
  detecting each failure in complying with the hygiene procedure;
  receiving feedback information from the analysis center (the feedback information produced automatically by the data analysis center and/or by one or more persons such as the management); and
  presenting the feedback information (e.g., confirmation of compliance, reminder and/or instructions for actions by the user, and/or warnings related to each failure in complying with the hygiene procedure as detected by the application or the analysis center).

The above is not an exhaustive list, and other related functions may be included as determined by those skilled in the art.

Some non-limiting examples (Examples 1-50) of the present subject matter are provided as follows:

In Example 1, a system for cleaning and sanitizing a box configured to be carried by a user may include a hygiene device. The hygiene device may be configured to be attached to the box, and may include an agent container configured to contain a hygiene agent, a spray nozzle configured to be inserted into the box (or otherwise placed in the box to perform its function), a pump in fluid communication with the agent container and in fluid communication with the spray nozzle, and a control circuit. The pump may be configured to pump the hygiene agent through the spray nozzle to produce a mist of the hygiene agent in the box. The control circuit may be configured to control hygiene cycles and may include a communication circuit configured to transmit and receive information, a hygiene cycle management circuit configured to initiate each cycle of the hygiene cycles, and a monitoring circuit configured to record information related to performance of each cycle of the hygiene cycles and to transmit the recorded information out of the hygiene device through the communication circuit.

In Example 2, the subject matter of Example 1 may optionally be configured such that the hygiene agent includes a cleaning agent.

In Example 3, the subject matter of Example 1 may optionally be configured such that the hygiene agent includes a sanitization agent.

In Example 4, the subject matter of Example 1 may optionally be configured such that the hygiene agent includes a cleaning and sanitization agent.

In Example 5, the subject matter of any one or any combination of Examples 1 to 4 may optionally be configured such that the hygiene cycle management circuit is further configured to control the pumping of the hygiene agent during each cycle of the hygiene cycles.

In Example 6, the subject matter of Example 5 may optionally be configured such that the hygiene cycle management circuit is configured to time the pumping of the hygiene agent and end the pumping of the hygiene agent when a specified time interval expires.

In Example 7, the subject matter of any one or any combination of Examples 1 to 6 may optionally be configured to further include a power source including one or more batteries.

In Example 8, the subject matter of Example 1 may optionally be configured such that the control circuit further includes a power management circuit coupled to the power source to monitor for a need to replace or recharging the one or more batteries.

In Example 9, the subject matter of any one or any combination of Examples 1 to 8 may optionally be configured to further include the box being a portable food delivery box.

In Example 10, the subject matter of any one or any combination of Examples 1 to 9 may optionally be configured such that the box has a flat bottom, and the spray nozzle is configured to be incorporated into a center of the bottom.

In Example 11, the subject matter of Example 10 may optionally be configured such that the box is a rectangular box having the flat bottom, a flat lid, four flat sides each coupled between the flat bottom and the flat lid when the lid is closed. The box includes one or more hinges connecting between the lid and one side of the four sides and a locking mechanism configured to lock the lid in a closed position.

In Example 12, the subject matter of any one or any combination of Examples 1 to 11 may optionally be configured such that the hygiene device is configured to be detachably attached to the box.

In Example 13, the subject matter of Example 12 may optionally be configured such that the hygiene device includes a container unit including the agent container, a controller unit including the diaphragm pump, the control circuit, and a battery, tubing coupled between the container and the controller box to provide for the fluid communication between the agent container and the pump, and tubing between the controller unit and the spray nozzle to provide for the fluid communication between the pump and the spray nozzle. The container unit and the controller unit are each configured to be detachably attached to the box.

In Example 14, the subject matter of any one or any combination of Examples 1 to 13 may optionally be configured such that the agent container comprises a refillable bottle.

In Example 15, the subject matter of any one or any combination of Examples 1 to 14 may optionally be configured such that the hygiene cycle management circuit is configured to initiate the hygiene cycles according to a specified schedule.

In Example 16, the subject matter of Example 15 may optionally be configured such that the hygiene cycle management circuit is configured to initiate the hygiene cycles periodically.

In Example 17, the subject matter of any one or any combination of Examples 1 to 16 may optionally be configured such that the hygiene cycle management circuit is configured to initiate each cycle of the hygiene cycles in response to a user command.

In Example 18, the subject matter of Example 17 may optionally be configured such that the hygiene cycle management circuit is configured to receive the user command through the communication circuit.

In Example 19, the subject matter of any one or any combination of Examples 11 to 18 may optionally be configured such that the hygiene cycle management circuit is configured to confirm that the box is empty and that the lid is closed and to start spraying a hygiene agent upon the confirmation.

In Example 20, the subject matter of Example 19 may optionally be configured such that the hygiene cycle management circuit is configured to transmit a confirmation request signal for confirming that the box is empty and that the lid is closed, to receive a confirmation response signal confirming in response to the transmission of the confirmation request signal, and to cause the spray nozzle and the pump to start spraying the hygiene agent upon receiving the confirmation response signal.

In Example 21, the subject matter of any one or any combination of Examples 1 to 20 may optionally be configured such that the monitoring circuit is further configured to notify the user the status of each hygiene cycle of the hygiene In Example 22, the subject matter of Example 21 may optionally be configured such that the monitoring circuit is further configured to notify the user to perform one or more functions during each hygiene cycle of the hygiene cycles according to a hygiene procedure.

In Example 23, the subject matter of any one or any combination of Examples 1 to 22 may optionally be configured such that the monitoring circuit is configured to record information including one or more of information identifying the box, information identifying the user, and timing information for each hygiene cycle of the hygiene cycles.

In Example 24, the subject matter of any one or any combination of Examples 1 to 23 may optionally be configured such that the monitoring circuit is configured to transmit the recorded information out of the hygiene device using wireless communication technology.

In Example 25, the subject matter of any one or any combination of Examples 1 to 24 may optionally be configured to further include a user interface device configured to present information related to each cycle of the hygiene cycles to the user and receive information related to the each cycle from the user.

In Example 26, the subject matter of Example 25 may optionally be configured such that the user interface device comprises a mobile device.

In Example 27, the subject matter of Example 26 may optionally be configured such that the mobile device comprises a cellphone and a hygiene application installed on the cellphone. The hygiene application allows the user to participate in control of each cycle of the hygiene cycles.

In Example 28, the subject matter of any one or any combination of Examples 25 to 27 may optionally be configured such that the user interface device is configured to allow the user to initiate a cycle of the hygiene cycles.

In Example 29, the subject matter of any one or any combination of Examples 25 to 27 may optionally be configured such that the user interface device is configured to allow the user to start spraying of the hygiene agent during each cycle of the hygiene cycles.

In Example 30, the subject matter of any one or any combination of Examples 25 to 29 may optionally be configured such that the user interface device is configured to receive the recorded information from the hygiene circuit.

In Example 31, the subject matter of Example 30 may optionally be configured to further include an analysis center configured to be communicatively coupled to the user interface device via wireless communication and to analyze the recorded information and produce feedback information based on an outcome of the analysis. The user interface device is configured to relay the recorded information to the analysis center and to receive the feedback information from the analysis center.

In Example 32, a method for cleaning and sanitizing a box configured to be carried by a user is provided. The method may include verifying emptiness of the box, starting an automatic hygiene cycle using a battery-powered portable hygiene device attached to the box, recording information related to performance of the hygiene cycle, and transmitting the recorded information to an analysis center for analysis and monitoring of hygiene status of the box.

In Example 33, the subject matter of starting the hygiene cycle as found in Example 32 may optionally include spraying a hygiene agent into the box to produce a mist of the hygiene agent in the box to result in substantially uniform distribution of the hygiene agent on interior surfaces of the box.

In Example 34, the subject matter of spraying the hygiene agent as found in Example 33 may optionally include spraying a cleaning agent.

In Example 35, the subject matter of spraying the hygiene agent as found in Example 33 may optionally include spraying a sanitization agent.

In Example 36, the subject matter of spraying the hygiene agent as found in Example 33 may optionally include spraying a cleaning and sanitization agent.

In Example 37, the subject matter of spraying the hygiene agent into the box as found in Example 33 may optionally include spraying the hygiene agent into the box using a single nozzle positioned at a bottom of the box.

In Example 38, the subject matter of any one or any combination of Examples 32 to 37 may optionally further include using a user interface device to communicate with the user regarding the hygiene cycle.

In Example 39, the subject matter of using the user interface device as found in Example 38 may optionally include using a cellphone carried by the user.

In Example 40, the subject matter of transmitting the recorded information to the analysis center as found in any one or any combination of Examples 38 and 39 may optionally further include transmitting the recorded information through a network using a wireless communication technology.

In Example 41, the subject matter of Example 40 may optionally further include producing instructions for the user based on the analysis and monitoring of hygiene status of the box and presenting the instruction for the user using the user interface device.

In Example 42, the subject matter of any one or any combination of Examples 38 to 41 may optionally further include verifying emptiness of the box comprises instructing the user to verify that the box is free of solid or liquid waste resulting from food delivery. The box is a food delivery box.

In Example 43, the subject matter of verifying emptiness of the box as found in Example 38 may optionally include instructing the user to verify the emptiness of the box.

In Example 44, the subject matter of starting the automatic hygiene cycle as found in any one or any combination of Examples 38 to 43 may optionally include starting the automatic hygiene cycle in response to a command transmitted from the application upon verification that the box is empty.

In Example 45, the subject matter of starting the automatic hygiene cycle as found in Example 34 may optionally include starting the automatic hygiene cycle according to a specified schedule and upon verification that the box is empty.

In Example 46, the subject matter of starting the automatic hygiene cycle as found in Example 45 may optionally include starting the automatic hygiene cycle on a periodic basis and upon verification that the box is empty.

In Example 47, the subject matter of any one or any combination of Examples 33 to 46 may optionally further include starting, timing, and ending the spray of the hygiene according to a specified time interval.

In Example 48, the subject matter of Example 47 may optionally further include using the user interface device to instruct the user to dry interior surfaces of the box upon completion of the hygiene cycle.

In Example 49, the subject matter of any one or any combination of Examples 33 to 46 may optionally further include using the user interface device to instruct the user to dry interior surfaces of the box upon completion of the hygiene cycle.

In Example 50, the subject matter of any one or any combination of Examples 33 to 49 may optionally further include using the user interface device to instruct the user to clean exterior surfaces of the box periodically.

This application is intended to cover adaptations or variations of the present subject matter. It is to be understood that the above description (including the list of examples 1-50) is intended to be illustrative, and not restrictive. The scope of the present invention should be determined with reference to the appended claims, along with the full scope of legal equivalents to which such claims are entitled.

What is claimed is:

1. A method for hygiene of a portable food delivery box, comprising:
 performing a hygiene cycle using a portable hygiene device attached to the portable food delivery box, the performance of the hygiene cycle including spraying a hygiene agent into the portable food delivery box;
 controlling the performance of the hygiene cycle using a control circuit of the portable hygiene device, including determining a location of the portable hygiene device and determining whether to initiate the hygiene cycle using criteria including the location of the portable hygiene device and whether the portable food delivery box is empty and closed; and recording information related to performance of the hygiene cycle using the control circuit.

2. The method of claim 1, wherein spraying the hygiene agent into the portable food delivery box comprises producing a mist of the hygiene agent in the portable food delivery box.

3. The method of claim 2, wherein spraying the hygiene agent comprises spraying a cleaning and sanitization agent.

4. The method of claim 3, wherein controlling the performance of the hygiene cycle using the control circuit comprises initiating a cycle of the hygiene cycles according to a programmed schedule.

5. The method of claim 3, wherein controlling the performance of the hygiene cycle using the control circuit further comprises initiating a cycle of the hygiene cycles in response to a user command overriding the programmed schedule.

6. The method of claim 1, further comprising tracking the location of the portable hygiene device to monitor deployment of the portable hygiene device in compliance of a hygiene procedure.

7. The method of claim 1, wherein recording the information related to performance of the hygiene cycle using the control circuit comprises recording a time of each cycle of the hygiene cycles.

8. The method of claim 7, wherein recording info], ration related to performance of the hygiene cycle using the control circuit comprises:
   determining a location where each cycle of the hygiene cycles is performed; and
   recording the location where the each cycle is performed.

9. The method of claim 1, further comprising determining whether the portable food delivery box is empty and closed, including:
   transmitting a confirmation request to a user interface device; and
   receiving a response signal from the user interface device, the response signal confirming that the portable food delivery box is empty and closed.

10. The method of claim 9, wherein transmitting the confirmation request to the user interface device comprises transmitting the confirmation request to a cellphone, and receiving the response signal from the user interface device comprises receiving the response signal from the cellphone.

11. An apparatus for hygiene of a portable food delivery box, comprising:
   a portable hygiene device configured to be attached to the portable food delivery box to perform hygiene cycles, the portable hygiene device including:
   a spray nozzle configured to spray a hygiene agent into the portable food delivery box;
   an agent container configured to contain the hygiene agent;
   a pump configured to be connected to the agent container and the spray nozzle to pump the hygiene agent from the agent container to the spray nozzle; and
   a control circuit configured to determine a location of the portable hygiene device to control the performance of the hygiene cycles and to record information related to the performance of each cycle of the hygiene cycles, the performance of the hygiene cycles including:
   initiation of each cycle of the hygiene cycles based on criteria including the location of the portable hygiene device and whether the portable food delivery box is empty and closed; and
   the pumping of the hygiene agent during the each cycle.

12. The apparatus of claim 11, wherein the spray nozzle comprises one or more spray nozzles configured and arranged to provide a mist of the hygiene agent in the portable food delivery box for uniform distribution of the hygiene agent over interior surfaces of the portable food delivery box.

13. The apparatus of claim 11, wherein the agent container comprises a disposable bottle.

14. The apparatus of claim 11, wherein the portable hygiene device is configured to be detachably attached to the portable food delivery box.

15. The apparatus of claim 11, wherein the portable hygiene device is battery-powered and comprises:
   a rechargeable battery; and
   a power management circuit configured to monitor a remaining level of the rechargeable battery and produce a battery level alert signal indicative of the remaining level of the rechargeable battery.

16. The apparatus of claim 15, wherein the control circuit is configured to record the location where each cycle of the hygiene cycles is performed.

17. The apparatus of claim 16, wherein the control circuit is configured to initiate the spray of the hygiene agent according to a programmed schedule and the location of the portable hygiene device.

18. The apparatus of claim 17, wherein the control circuit is further configured to receive a user command and to start the spray of the hygiene agent in response to the user command.

19. An apparatus for hygiene of a portable food delivery box, comprising:
   a portable hygiene device configured to be attached to the portable food delivery box to perform hygiene cycles, the portable hygiene device including:
   means for spraying a hygiene agent into the portable food delivery box; and
   means for controlling the performance of the hygiene cycles including the spraying of the hygiene agent during each cycle of the hygiene cycles and for recording information related to the performance of the each cycle, including means for determining whether the portable food delivery box is empty and closed and starting the spraying of the hygiene agent upon determination that the portable food delivery box is empty and closed.

20. The apparatus of claim 19, where the portable hygiene device further comprises:
   means for providing electric power used for the performance of the hygiene cycles; and
   means for managing operation of the means for providing the electric power.

* * * * *

UNITED STATES PATENT AND TRADEMARK OFFICE
CERTIFICATE OF CORRECTION

PATENT NO. : 11,911,529 B2
APPLICATION NO. : 17/656566
DATED : February 27, 2024
INVENTOR(S) : Wei et al.

Page 1 of 1

It is certified that error appears in the above-identified patent and that said Letters Patent is hereby corrected as shown below:

In the Claims

In Column 15, Line 28, in Claim 8, delete "info], ration" and insert --information-- therefor Signed and Sealed this
Fourth Day of March, 2025

Coke Morgan Stewart
*Acting Director of the United States Patent and Trademark Office*